US009079875B2

(12) United States Patent
Goossen et al.

(10) Patent No.: US 9,079,875 B2
(45) Date of Patent: Jul. 14, 2015

(54) METHOD FOR DECARBOXYLATING C—C CROSS-LINKING OF CARBOXYLIC ACIDS WITH CARBON ELECTROPHILES

(75) Inventors: Lukas Goossen, Kaiserslautern (DE); Guojun Deng, Metairie, LA (US)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 745 days.

(21) Appl. No.: 11/913,626

(22) PCT Filed: May 10, 2006

(86) PCT No.: PCT/DE2006/001014
§ 371 (c)(1),
(2), (4) Date: Nov. 5, 2007

(87) PCT Pub. No.: WO2006/136135
PCT Pub. Date: Dec. 28, 2006

(65) Prior Publication Data
US 2008/0177114 A1 Jul. 24, 2008

(30) Foreign Application Priority Data
May 10, 2005 (DE) .......................... 10 2005 022 362

(51) Int. Cl.
| | | |
|---|---|---|
| C07C 63/00 | (2006.01) | |
| C07C 65/00 | (2006.01) | |
| C07C 61/00 | (2006.01) | |
| C07C 61/08 | (2006.01) | |
| C07C 19/00 | (2006.01) | |
| C07C 2/66 | (2006.01) | |
| C07C 5/09 | (2006.01) | |
| C07C 15/40 | (2006.01) | |
| C07C 2/26 | (2006.01) | |
| C07D 333/08 | (2006.01) | |
| B01J 31/18 | (2006.01) | |
| B01J 31/22 | (2006.01) | |
| B01J 31/24 | (2006.01) | |
| B01J 31/26 | (2006.01) | |
| C07B 37/04 | (2006.01) | |
| C07C 1/26 | (2006.01) | |
| C07C 17/263 | (2006.01) | |
| C07C 17/266 | (2006.01) | |
| C07C 41/30 | (2006.01) | |
| C07C 45/68 | (2006.01) | |
| C07C 45/72 | (2006.01) | |
| C07C 201/12 | (2006.01) | |
| C07C 209/68 | (2006.01) | |
| C07C 231/12 | (2006.01) | |
| C07C 253/30 | (2006.01) | |
| C07C 315/04 | (2006.01) | |
| C07C 319/20 | (2006.01) | |
| B01J 27/122 | (2006.01) | |
| B01J 27/232 | (2006.01) | |

(52) U.S. Cl.
CPC ............. *C07D 333/08* (2013.01); *B01J 31/183* (2013.01); *B01J 31/1815* (2013.01); *B01J 31/2234* (2013.01); *B01J 31/2404* (2013.01); *B01J 31/26* (2013.01); *C07B 37/04* (2013.01); *C07C 1/26* (2013.01); *C07C 17/263* (2013.01); *C07C 17/266* (2013.01); *C07C 17/2637* (2013.01); *C07C 41/30* (2013.01); *C07C 45/68* (2013.01); *C07C 45/72* (2013.01); *C07C 201/12* (2013.01); *C07C 209/68* (2013.01); *C07C 231/12* (2013.01); *C07C 253/30* (2013.01); *C07C 315/04* (2013.01); *C07C 319/20* (2013.01); *B01J 27/122* (2013.01); *B01J 27/232* (2013.01); *B01J 2231/4205* (2013.01); *B01J 2531/0241* (2013.01); *B01J 2531/16* (2013.01); *B01J 2531/17* (2013.01); *B01J 2531/824* (2013.01); *C07C 2103/26* (2013.01); *C07C 2527/122* (2013.01); *C07C 2531/24* (2013.01); *C07C 2531/28* (2013.01); *C07C 2531/30* (2013.01)

(58) Field of Classification Search
None
See application file for complete search history.

(56) References Cited

U.S. PATENT DOCUMENTS

| | | | | |
|---|---|---|---|---|
| 4,786,714 | A * | 11/1988 | Drent ............................. | 528/392 |
| 5,858,907 | A * | 1/1999 | Wang et al. ................... | 502/213 |
| 6,218,564 | B1 * | 4/2001 | Monteith ....................... | 558/378 |
| 2009/0221832 | A1 * | 9/2009 | Cotte et al. ................... | 546/315 |

FOREIGN PATENT DOCUMENTS

| | | |
|---|---|---|
| EP | 0 606 065 A1 | 7/1994 |
| WO | 97 33846 A | 9/1997 |

OTHER PUBLICATIONS

Frisch et al., Angewandte Chemie Internation Edition, 2005, vol. 44 (5), pp. 674-688.*

(Continued)

*Primary Examiner* — Clinton Brooks
(74) *Attorney, Agent, or Firm* — Norris McLaughlin & Marcus, P A

(57) ABSTRACT

The invention relates to a method for decarboxylating C—C bond formation by reacting carboxylic salts with carbon electrophiles in the presence of transition metal compounds as catalysts. The method represents a decarboxylating C—C bond formation of carboxylic acid salts with carbon electrophiles, wherein the catalyst contains two transition metals and/or transition metal compounds, from which one is present, preferably, in the oxidation step, which are different from each other by one unit, and catalyzes a radical decarboxylation which is absorbed during the second oxidation steps, which are different from each other by two units and catalyzes the two electron processes of a C—C bond formation reaction.

12 Claims, No Drawings

(56) References Cited

OTHER PUBLICATIONS

Lemaire et al. Tetrahedron Letters 41 (2000) 8791-8794.*
Negishi et al. Chem. Rev. 2003, 103, 1979-2017.*
Cohen et al. Journal of the American Chemical Society 1970, 3189-3190.*
Meyers, A.G. et al J. Am. Chem. Soc. 2002, 124, 11250-11251.*
Miura, M et al. J. Am. Chem. Soc., 2002, 124, 5286-5287.*
Nilsson, M.; "A New Biaryl Synthesis Illustrating a Connection between the Ullmann Biaryl Synthesis and Copper-catalysed Decarboxylation"; Acta Chemica Scandinavica 20, 1966; pp. 423-426.
Rodriguez, J. et al; "An Efficient One-Pot Preparation of 2,4-Pentadienoic Esters from alpha, beta-Unsaturated Aldehydes"; Communications, Synthesis, 7, 1988, pp. 534-535.
Yamanaka, H., et al; "Influence of Heteroaromatic Amines to Knoevenagel Condensation"; Heterocycles, vol. 20, No. 8, 1983; pp. 1541-1544.
Patent Abstracts of Japan; vol. 12, No. 172, 1988 (JP 62 281840 ; A. Otsuka Pharmaceut Co Ltd.)
Narsaiah, A.V., et al; "An Eco-Friendly Synthesis of Electrophilic Alkenes Catalyzed by Dimethylaminopyridine Under solvent-Free Conditions"; Synthetic Communications; vol. 34, No. 16, pp. 2893-2901, 2004.
Guyot, J., et al; "Cinetique et mecanisme de la reaction de knoevenagel dans le benzene-2"; Tetrahedron, vol. 39, No. 7, 1983, pp. 1167-1179 (English Abstract on p. 1).
Database Beilstein: Summary, Journal Dell'Orco et al, Anchem, Anal. Chem. EN, 71, 22, 1999, pp. 5165-5170 XP-002402407.
New, J. S.; et al; "The Thieno[3,2-c]pyridine and Furo[3,2-c]pyridine Rings: New Pharmacophores with Potential Antipsychotic Activity"; J. Med. Chem. 1989, vol. 32, No. 6, pp. 1147-1156.
Ragoussis, N et al; "Improvement on the synthesis of (E)-alk-3-enoic acids"; J. Chem. Soc., Perkin Trans., 1, 1998, pp. 3529-3533.
List, B. et al; "A Practical, efficient, and atomic economic alternative to the Wittig and Horner-Wadsworth-Emmons reactions for the synthesis of (E)-alpha, beta-unsaturated esters from aldehydes": Tetrahedron, 62, 2006, pp. 476-482.
Cohen et al; "Products and Kinetics of Decarboxylation of Activated and Unactivated Aromatic Cuprous Carboxylates in Pyridine and in Quinoline"; J. Org. Chem. vol. 43, No. 5, 1978; pp. 837-848.
Cohen et al; "The Copper-Quinoline Decarboxylation"; Journal of the American Chemical Society, 92:10, Mar. 20, 1970, pp. 3189-3190.

* cited by examiner

METHOD FOR DECARBOXYLATING C—C CROSS-LINKING OF CARBOXYLIC ACIDS WITH CARBON ELECTROPHILES

This application is a 371 of PCT/DE2006/001014, filed May 10, 2006, which claims foreign priority benefit under 35 U.S.C. §119 of the German Patent Application No. 10 2005 022 362.1 filed May 10, 2005.

The invention relates to a process for C—C bond formation of carbon nucleophiles which are formed by decarboxylation from carboxylic acid salts with carbon electrophiles in the presence of transition metal catalysts.

The biaryl substructure is a key functionality in functional materials, pharmaceuticals and crop protection preparations. For the synthesis of such compounds, the Suzuki coupling of aryl halides with boronic acids in particular is utilized, since it can be performed in a simple manner and in excellent yields, and many functional groups and substitution patterns are tolerated. Of particular interest is the compound 2-nitro-4'-chlorobiphenyl, an intermediate in the preparation of the fungicide boscalid. Its industrial preparation is shown in scheme 1 as an example of a Suzuki coupling.

Scheme 1. Suzuki coupling

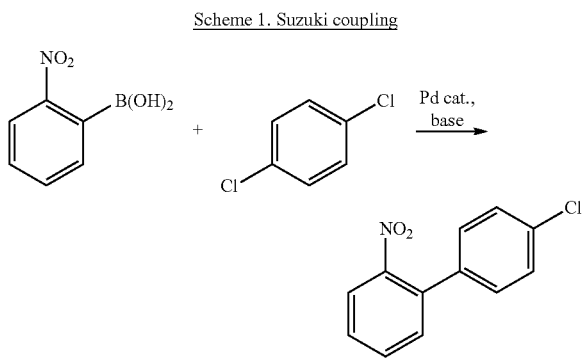

Especially for industrial applications, this procedure, however, has serious disadvantages owing to the difficult obtainability and the resulting high cost of boronic acids. Their synthesis by metallating vinyl and aryl halides and subsequently reacting with trialkyl borates is complicated and not compatible with all functional groups. More widely usable are catalytic cross-coupling reactions of organohalides with diboron compounds, but they find barely any industrial use owing to the high cost of this compound. The preparation of boronic acids from pinacol- or catecholborane is also industrially not very attractive owing to the high costs.

Other biaryl syntheses are distinctly inferior to the Suzuki coupling with regard to yield, performability and application breadth. For example, the Scholl reaction, in which two arenas are reacted with one another in the presence of a Lewis acid and of a Brønsted acid, affords generally only unsatisfactory yields and is compatible only with a few functional groups. The same applies to the Gomberg-Bachmann reaction. More widely usable is the Ullmann reaction, in which two aryl iodides are coupled to one another in the presence of copper compounds, but only the synthesis of symmetric compounds succeeds in satisfactory yield.

Catalytic cross-coupling reactions with magnesium aryls, zinc aryls or lithium aryls are less advantageous than the Suzuki reaction owing to the difficult handling of these compounds and their low compatibility with functional groups. Only arylsiloxanes and the toxic arylstannanes exhibit similarly good properties such as arylboronic acids, but the preparation of these compounds also gives rise to the same problems.

There is thus a need for novel cross-coupling reactions proceeding from carbon nucleophiles which are notable for good availability and handling, and a low cost. Metal salts of carboxylic acids are widely available and are therefore ideal starting materials. A coupling reaction in which organometallic species are generated in situ by decarboxylating carboxylic acid salts and coupled to carbon electrophiles is therefore of high interest, especially when they can also be utilized to obtain biaryls.

To date, there is only one example of a related reaction, in which the pyrolysis of copper carboxylates in the presence of excess aryl halide, as a constituent of a complex reaction mixture, forms the corresponding biaryl among other products. The extreme temperatures (240° C.), the low yields, the large amounts of copper salts and the restricted substrate range, however, make this reaction unsuitable for commercial utilization.

It was an object of the present invention to develop a generally employable, catalytic process for cross-coupling carbon nucleophiles with carbon electrophiles, in which the carbon nucleophiles are formed in situ by decarboxylating metal carboxylates. The particular difficulty consisted in the finding of a suitable catalyst system, since a decarboxylation of carboxylic acids is effected typically via a free-radical mechanism, while the reason for the efficiency of cross-coupling catalysts is that they selectively promote only two-electron processes and suppress free-radical reaction steps.

The present invention provides a process for decarboxylating C—C bond formation by reacting carboxylic acid salts with carbon electrophiles in the presence of transition metals or transition metal compounds as a catalyst.

Scheme 2. Inventive decarboxylating cross-coupling of carboxylates and carbon electrophiles.

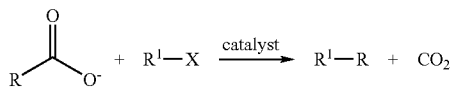

It has been found that, surprisingly, a catalyst system which comprises two or more metal compounds can very efficiently catalyze the decarboxylating cross-coupling of carboxylic acid salts with carbon electrophiles according to scheme 2.

The catalyst system preferably comprises at least two different transition metal compounds. Particularly suitable systems are those in which the first transition metal can assume oxidation states which differ by one unit, and the second can assume oxidation states which differ from one another by two units. It is assumed that the first transition metal catalyzes a free-radical decarboxylation, while the second catalyzes the two-electron processes of a cross-coupling reaction. Surprisingly, these simultaneous catalytic processes do not disrupt one another; it is suspected that the catalyst components mutually enhance their action, such that the decarboxylation step, even in the case of extremely small amounts of catalyst, proceeds even at unprecedentedly low temperatures.

When two or more different transition metals or transition metal compounds are used, depending on the substrate used, it is possible to use the first metal compound as the first catalyst component in stoichiometric amounts and the second metal or metal compound as the second catalyst component in catalytic amounts.

Additionally found has been a process in which this catalyst system is used, which is characterized in that carboxylic acid salts are converted to carbon nucleophiles with extrusion of carbon dioxide and linked to carbon electrophiles to form a C—C bond.

What is advantageous over the prior art described is that carboxylic acid salts are much less expensive, more readily available and easier to handle than organometallic compounds, for example boronic acids. The advantages of the novel catalyst over that described by Nilsson arise from the fact that the inventive catalyst system is formed by adding a second metal component which specifically catalyzes the cross-coupling. In this way, a much greater substrate breadth can be converted at much lower temperatures in unprecedented high selectivities and yields. In addition, only catalytic amounts of transition metals are required, while the process of Nilsson absolutely requires stoichiometric amounts of copper.

The inventive catalyst system preferably comprises two metal components. The first component preferably comprises metal which can assume two oxidation states which differ by one unit, preferably from the group of Ag (0,I), Cu (0,I,II), Mn (II,III), Fe (II,III), Co (II,III), Ni (II,III), Mo (IV,V), Ru (II,III) (examples of suitable combinations of oxidation states in brackets). The metal may, as desired, be used in elemental form, as a complex or as a salt. Particular preference is given to using copper or silver compounds, and very particular preference to using copper(I) compounds.

The second component is characterized in that it contains a metal which can assume two oxidation states which differ by two units, preferably from the group of Pd (0,II), Ni (0,II), Fe (−II,0,II), Au (I,III), Rh (I,III), Pt (0,II,IV), Ru (0,II), Ir (I,III) (examples of suitable combinations of oxidation states in brackets). The metal may, as desired, be used in elemental form, as a complex or as a salt. Particular preference is given to using platinum group metals, very particular preference to using palladium compounds and even greater preference to using palladium(II) acetylacetonate.

The two metals may each independently, if desired, be stabilized by further ligands, preferably from the group of amines, phosphines, N-heterocyclic carbenes, nitriles or olefins. Particular preference is given to using cyclic amines as ligands; very particular preference is given to using chelating cyclic amines from the group of phenanthroline, bipyridine and terpyridine or their substituted derivatives.

The actual catalysts can optionally be obtained in the reaction mixture from suitable metal precursors by the addition of the components listed above.

In the process according to the invention, it is possible to use carboxylic acid salts of the general formula I where n, m, q, p are numbers from 1 to 6 and r is a number from 0 to 6.

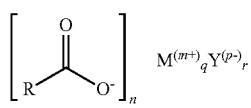

I

The counterion $M^{(n+)}$ is either a metal cation, preferably from the group of the metals Li, Na, K, Mg, Ca, B, Al, Ag, Cu, Mn, Fe, Co, Ni, Mo, Ru or an organic cation, preferably from the group of ammonium, pyridinium, phosphonium. It may be possible for a further anion to be coordinated in addition to the carboxylate, preferably from the group of $I^-$, $Br^-$, $Cl^-$, $F^-$, $CO_3^-$, $CN^-$, $OH^-$, $OAlkyl^-$, $HCO_3^-$, $PO_4^{3-}$, $HPO_4^{2-}$, $H_2PO_4^-$.

The carboxylic acid salts are either added in preformed form or generated in situ from the carboxylic acids and suitable bases.

The substituent R is an organic radical and can preferably be selected from the group of linear, branched and cyclic $C_1$-$C_{20}$-alkyl, linear, branched and cyclic $C_2$-$C_{20}$-alkenyl, and also $C_6$-$C_{20}$-aryl and heteroaryl from the group of pyridine, pyrimidine, pyridazine, pyrazine, triazine, tetrazine, pyrrole, pyrazole, isoxazole, imidazole, oxazole, thiazole, thiophene, furan, and may in turn bear further substituents from the group of linear, branched and cyclic $C_1$-$C_{10}$-alkyl, linear, branched and cyclic $C_2$-$C_{20}$-alkenyl, and also $C_6$-$C_{10}$-aryl and heteroaryl, linear, branched and cyclic $C_1$-$C_{10}$-alkyloxy or $C_1$-$C_{10}$-aryloxy, linear, branched and cyclic $C_1$-$C_{10}$-alkyl- or $C_1$-$C_{10}$-arylaminocarbonyl, linear, branched and cyclic $C_1$-$C_{10}$-acyl, linear, branched and cyclic $C_1$-$C_{10}$-dialkylamino, $C_1$-$C_{10}$-arylamino, formyl, oxo, thio, hydroxyl, carboxyl, nitro, cyano, nitroso, and halogens such as F, Cl, Br and I.

R can more preferably be selected from the group of linear, branched and cyclic $C_2$-$C_{10}$-alkenyl, $C_6$-$C_{10}$-aryl or heteroaryl from the group of pyridine, pyrimidine, pyridazine, pyrazine, triazine, tetrazine, pyrrole, pyrazole, isoxazole, imidazole, oxazole, thiazole, thiophene, furan, and may in turn bear further substituents as described in the preceding paragraph.

$$R^1—X \quad (II)$$

In the carbon electrophile $R^1$—X (formula II), the substituent X is a common leaving group and can preferably be selected from the group of: halides and pseudohalides from the group of toluenesulfonate, methylsulfonate, trifluorosulfonate, trifluoroacetate, carboxylate and $[N_2]^+$.

In the process according to the invention, the substituent $R^1$ of the carbon electrophile (formula II) is an organic radical and can preferably be selected from the group of linear, branched and cyclic $C_1$-$C_{20}$-alkyl, linear, branched and cyclic $C_2$-$C_{20}$-alkenyl, and also $C_6$-$C_{20}$-aryl and heteroaryl from the group of pyridine, pyrimidine, pyridazine, pyrazine, triazine, tetrazine, pyrrole, pyrazole, isoxazole, imidazole, oxazole, thiazole, thiophene, furan, and may in turn bear further substituents from the group of linear, branched and cyclic $C_1$-$C_{10}$-alkyl, linear, branched and cyclic $C_2$-$C_{20}$-alkenyl, and also $C_6$-$C_{10}$-aryl and heteroaryl, linear, branched and cyclic $C_1$-$C_{10}$-alkyloxy or $C_1$-$C_{10}$-aryloxy, linear, branched and cyclic $C_1$-$C_{10}$-alkyl- or $C_1$-$C_{10}$-arylaminocarbonyl, linear, branched and cyclic $C_1$-$C_{10}$-acyl, linear, branched and cyclic $C_1$-$C_{10}$-dialkylamino, $C_1$-$C_{10}$-arylamino, formyl, oxo, thio, hydroxyl, carboxyl, nitro, cyano, nitroso, and halogens such as F, Cl, Br and I.

$R^1$ can more preferably be selected from the group of linear, branched and cyclic $C_2$-$C_{10}$-alkenyl, $C_6$-$C_{10}$-aryl or heteroaryl from the group of pyridine, pyrimidine, pyridazine, pyrazine, triazine, tetrazine, pyrrole, pyrazole, isoxazole, imidazole, oxazole, thiazole, thiophene, furan, and may in turn bear further substituents as described in the preceding paragraph.

Alternatively, the carbon electrophile may be a carbonyl derivative, preferably from the group of carbonyl chloride, carboxylic anhydride, aldehyde, ketone, ester, α,β-unsaturated aldehyde, α,β-unsaturated ketone, α,β-unsaturated ester.

In the process according to the invention, the two catalysts are each independently used in amounts of from 0.001 mol % to 100 mol % based on the carbon electrophile; preference is given to using amounts of from 0.001 mol % to 10 mol % and particular preference to amounts of from 0.01 mol % to 5 mol %.

The process according to the invention is performed at temperatures of from 20° C. to 220° C., preferably at from 80° C. to 200° C. and more preferably at from 120° C. to 160° C.

The process according to the invention can be performed in the presence of a solvent or in substance. For example, the solvent used may be one of the feedstocks, linear, cyclic and branched hydrocarbons (for example hexanes, heptanes and octanes), aromatic hydrocarbons (for example benzene, toluene, xylenes, ethylbenzene, mesitylene), ethers (for example 1,4-dioxane, tetrahydrofuran, methyltetrahydrofuran, dibutyl ether, methyl t-butyl ether, diisopropyl ether, diethylene glycol dimethyl ether), esters (for example ethyl acetate, butyl acetate), amides (for example dimethylformamide, diethylformamide, N-methylpyrrolidone, dimethylacetamide), dimethyl sulfoxide, sulfolane, acetonitrile, isobutyronitrile, propionitrile, propylene carbonate and chlorinated aliphatic and aromatic hydrocarbons.

Preference is given to using dimethylformamide, diethylformamide, N-methylpyrrolidone, dimethylacetamide, dimethyl sulfoxide, sulfolane, acetonitrile and propylene carbonate.

The process according to the invention is preferably performed by removing traces of water during the reaction by customary methods, for example by distillation or by addition of water-binding media.

The present invention further provides a catalyst system for decarboxylating C—C bond formation of carboxylic acid salts with carbon electrophiles, consisting of two transition metals or transition metal compounds and an optionally substituted chelating cyclic amine from the group of phenanthroline, bipyridine and terpyridine. The transition metals are preferably selected from the so-called noble metals, especially from palladium or palladium compounds and copper or a copper compound.

Examples 1-18

It is evident from Examples 1-18 that a combination of copper(II) carbonate and palladium-phosphine complexes at particularly low temperatures of 120° achieves excellent yields of cross-coupling products. The transition metal compounds used are reduced to lower oxidation states in the reaction mixture. It is assumed that copper is present as Cu(I) compounds and palladium as Pd(0).

According to Table 1, in each case 1.5 mmol of o-nitrobenzoic acid were first deprotonated with a stoichiometric amount of the base. The resulting carboxylic acid salt was stirred with 1.0 mmol of 4-chloro-1-bromobenzene in the presence of a palladium(II) salt (0.02 mmol), optionally a ligand (0.06 mmol) and/or an additive (1.5 mmol) in 3 ml of a solvent at 120° C. for 24 h. In some cases, the reaction mixture was dried by adding 500 mg of molecular sieves (3 Å). The yields were determined with the aid of gas chromatography using n-tetradecane as an internal standard.

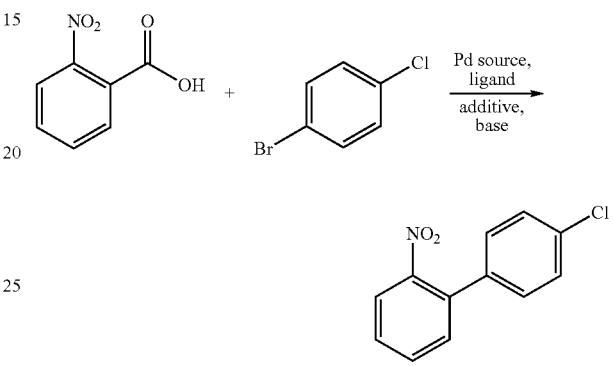

Scheme 3. Preparation of 2-nitro-4'-chlorobiphenyl

| Example | Pd source | Ligand | Solvent | Base | Additive | Yield (%) |
|---|---|---|---|---|---|---|
| 1 | Pd(acac)$_2$ | PPh$_3$ | NMP | CuCO$_3$ | — | 9 |
| 2 | PdCl$_2$ | PPh$_3$ | NMP | CuCO$_3$ | — | 3 |
| 3 | Pd(OAc)$_2$ | PPh$_3$ | NMP | CuCO$_3$ | — | 5 |
| 4 | Pd(acac)$_2$ | PPh$_3$ | NMP | CuCO$_3$ | KBr | 14 |
| 5 | Pd(acac)$_2$ | PPh$_3$ | NMP | CuCO$_3$ | NaF | 16 |
| 6 | Pd(acac)$_2$ | PPh$_3$ | NMP | CuCO$_3$ | LiF | 15 |
| 7 | Pd(acac)$_2$ | PPh$_3$ | NMP | CuCO$_3$ | KF | 32 |
| 8 | Pd(acac)$_2$ | PPh$_3$ | NMP | CuCO$_3$ | KF/3 Å MS | 84 |
| 9 | Pd(acac)$_2$ | BINAP | NMP | CuCO$_3$ | KF/3 Å MS | 76 |
| 10 | Pd(acac)$_2$ | DPPF | NMP | CuCO$_3$ | KF/3 Å MS | 70 |
| 11 | Pd(acac)$_2$ | P(p-MeOPh)$_3$ | NMP | CuCO$_3$ | KF/3 Å MS | 71 |
| 12 | Pd(acac)$_2$ | P(Cy)$_3$ | NMP | CuCO$_3$ | KF/3 Å MS | 60 |
| 13 | Pd(acac)$_2$ | Bipyridine | NMP | CuCO$_3$ | KF/3 Å MS | 35 |
| 14 | Pd(acac)$_2$ | P(i-propyl)Ph$_2$ | NMP | CuCO$_3$ | KF/3 Å MS | 98 |
| 15 | Pd(acac)$_2$ | P(i-propyl)Ph$_2$ | NMP | Ag$_2$CO$_3$ | KF/3 Å MS | 45 |
| 16 | Pd(acac)$_2$ | P(i-propyl)Ph$_2$ | DMSO | CuCO$_3$ | KF/3 Å MS | 69 |
| 17 | Pd(acac)$_2$ | P(i-propyl)Ph$_2$ | DMPU | CuCO$_3$ | KF/3 Å MS | 62 |
| 18 | Pd(acac)$_2$ | P(i-propyl)Ph$_2$ | Diglyme | CuCO$_3$ | KF/3 Å MS | 40 |

Examples 19-25

It is evident from Examples 19-25, Table 2, that, in a second process variant, the reaction of potassium carboxylates generated in situ with aryl halides, even with exceptionally small amounts of catalyst systems consisting of copper(I) salts, palladium(II) salts and amine ligands proceeds in high efficiency. In each case 1.5 mmol of o-nitrobenzoic acid were first deprotonated with a stoichiometric amount of potassium carbonate and the water of reaction was removed by distillation. The resulting carboxylic acid salt was then stirred with 1.0 mmol of 4-chloro-1-bromobenzene in the presence of 0.02 mmol of palladium(II) acetylacetonate, the specified amount of copper(I) halide and the specified amount of the amine ligand in NMP at 160° C. for 24 h. Any remaining moisture was bound by the addition of 500 mg of molecular sieves (3 Å). The yields were determined with the aid of gas chromatography using n-tetradecane as an internal standard.

Scheme 4

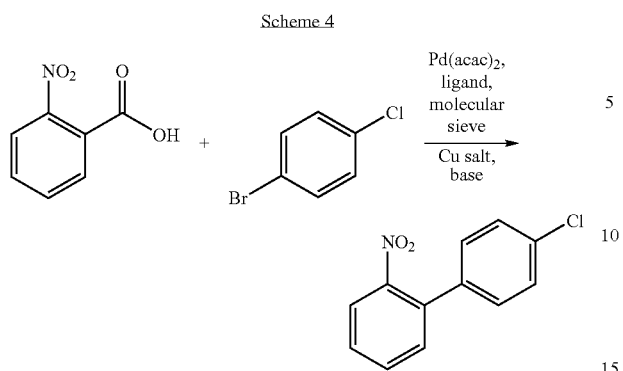

TABLE 2

| Example | Pd(acac)$_2$ (mmol) | Ligand (mmol) | Cu salt (mmol) | Yield (%) |
|---|---|---|---|---|
| 19 | 0.02 | Dipyridyl (0.1) | CuI (0.1) | 99 |
| 20 | 0.02 | Dipyridyl (0.1) | CuBr (0.1) | 95 |
| 21 | 0.02 | Dipyridyl (0.1) | CuCl (0.1) | 95 |
| 22 | 0.02 | 4,4'-Dimethyl-2,2'-dipyridyl (0.1) | CuI (0.1) | 98 |
| 23 | 0.02 | Phenanthroline (0.1) | CuI (0.1) | 99 |
| 24 | 0.01 | Phenanthroline (0.05) | CuI (0.03) | 97 |
| 25 | 0.005 | Phenanthroline (0.05) | CuI (0.01) | 80 |

Examples 26-55

Examples 26-55 from Table 3, which were performed according to scheme 5 on a scale of 1 mmol, demonstrate the wide applicability of the process according to the invention. To determine the yields, after aqueous workup, the products were chromatographed on silica gel and characterized unambiguously with the aid of NMR, MS, HRMS.

Scheme 5

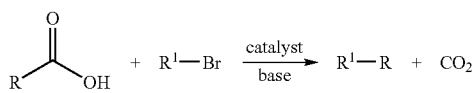

TABLE 3

| | R | R$^1$ | Conditions | Yield (%) |
|---|---|---|---|---|
| 26 | 2-nitrotoluene (NO$_2$, CH$_3$) | 4-chlorotoluene (Cl, CH$_3$) | Pd(acac)$_2$ (0.02 mmol), CuCO$_3$ (1.5 mmol), P(isopropyl)Ph$_2$ (0.06 mmol), KF (1.5 mmol), molecular sieves (3 Å, 500 mg), NMP (3 ml), 120°, 24 h | 98 |
| 27 | 2-nitrotoluene (NO$_2$, CH$_3$) | 4-cyanotoluene (NC, CH$_3$) | Pd(acac)$_2$ (0.02 mmol), CuCO$_3$ (1.5 mmol), P(isopropyl)Ph$_2$ (0.06 mmol), KF (1.5 mmol), molecular sieves (3 Å, 500 mg), NMP (3 ml), 120°, 24 h | 96 |
| 28 | 2-nitrotoluene (NO$_2$, CH$_3$) | p-xylene (H$_3$C, CH$_3$) | Pd(acac)$_2$ (0.02 mmol), CuCO$_3$ (1.5 mmol), P(isopropyl)Ph$_2$ (0.06 mmol), KF (1.5 mmol), molecular sieves (3 Å, 500 mg), NMP (3 ml), 120°, 24 h | 97 |

TABLE 3-continued

| | R | R¹ | Conditions | Yield (%) |
|---|---|---|---|---|
| 29 | 2-NO₂-C₆H₄- | 4-MeO-C₆H₄- | Pd(acac)₂ (0.02 mmol), CuCO₃ (1.5 mmol), P(isopropyl)Ph₂ (0.06 mmol), KF (1.5 mmol), molecular sieves (3 Å, 500 mg), NMP (3 ml), 120°, 24 h | 79 |
| 30 | 2-NO₂-C₆H₄- | 4-MeS-C₆H₄- | see Example 29 | 82 |
| 31 | 2-NO₂-C₆H₄- | 4-O₂N-C₆H₄- | see Example 29 | 95 |
| 32 | 2-NO₂-C₆H₄- | 4-H₃COC-C₆H₄- | see Example 29 | 86 |
| 33 | 2-NO₂-C₆H₄- | 4-C₂H₅OOC-C₆H₄- | see Example 29 | 97 |
| 34 | 2-NO₂-C₆H₄- | 4-OHC-C₆H₄- | see Example 29 | 93 |
| 35 | 2-NO₂-C₆H₄- | naphthalen-2-yl | see Example 29 | 94 |
| 36 | 2-NO₂-C₆H₄- | naphthalen-1-yl | see Example 29 | 88 |
| 37 | 2-NO₂-C₆H₄- | 2,4-(H₃C)₂-C₆H₃- | see Example 29 | 93 |
| 38 | 2-NO₂-C₆H₄- | 2-OMe-C₆H₄- | see Example 29 | 80 |

TABLE 3-continued

| | R | R¹ | Conditions | Yield (%) |
|---|---|---|---|---|
| 39 | 2-nitrotoluene | 9-methylphenanthrene | see Example 29 | 86 |
| 40 | 2-nitrotoluene | toluene | see Example 29 | 85 |
| 41 | 2-nitrotoluene | 4-propyltoluene | see Example 29 | 95 |
| 42 | 2-nitrotoluene | 4-methylbenzophenone | see Example 29 | 94 |
| 43 | 2-methylthiophene | p-xylene | Pd(acac)$_2$ (0.02 mmol), CuI (1.2 mmol), dipyridyl (0.1 mmol), K$_2$CO$_3$ (1.2 mmol), molecular sieves (3 Å, 500 mg), NMP (3 ml), 160°, 24 h | 82 |
| 44 | 4-methylanisole | p-xylene | Pd(acac)$_2$ (0.02 mmol), CuCO$_3$ (1.5 mmol), P(isopropyl)Ph$_2$ (0.06 mmol), KF (1.5 mmol), NMP (3 ml), 160°, 24 h | 46 |
| 45 | trans-β-methylstyrene | p-xylene | see Example 44 | 82 |
| 46 | trans-β-methylstyrene | 4-chlorotoluene | see Example 44 | 85 |
| 47 | trans-β-methylstyrene | 2,4-dimethyltoluene | see Example 44 | 88 |

TABLE 3-continued

| | R | R¹ | Conditions | Yield (%) |
|---|---|---|---|---|
| 48 | 2-methyl-(methylsulfonyl)benzene | 4-methylphenyl | see Example 43 | 97 |
| 49 | 2-fluorotoluene | 4-methylphenyl | see Example 43 | 82 |
| 50 | 2-methylacetophenone | 4-methylphenyl | see Example 43 | 83 |
| 51 | N-phenyl-2-methylaniline | 4-methylphenyl | see Example 43 | 91 |
| 52 | 2-methylacetanilide | 4-methylphenyl | see Example 43 | 30 |
| 53 | 2-methylanisole | 4-methylphenyl | see Example 43 | 29 |
| 54 | 2-methylbenzaldehyde | 4-methylphenyl | see Example 43 | 60 |
| 55 | (4-methoxyphenyl)(2-methylphenyl)methanone | 4-acetylphenyl | see Example 43 | 70 |

Examples with a Catalytic Amount of Copper and a Catalytic Amount of Palladium Examples 56-71 from Table 4, which were performed according to scheme 5 with 1 mmol of aryl bromide and 1.2 mmol of carboxylic acid, demonstrate that the two transition metals are required only in catalytic amounts irrespective of the substrates. To determine the yields, after aqueous workup, the products were chromatographed on silica gel and characterized unambiguously with the aid of NMR, MS, HRMS.

Scheme 5

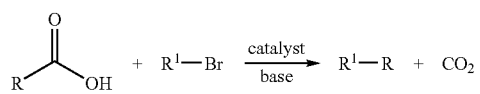

| | R | R¹ | Conditions | Yield (%) |
|---|---|---|---|---|
| 56 | 2-methylphenyl methyl ketone (H₃C-C(=O)- on 2-methylphenyl) | 4-methylphenyl (-C₆H₄-CH₃) | Cs₂CO₃ (1.2 mmol), CuCl (0.15 mmol), Pd(acac)₂ (0.02 mmol), 1,10-phenanthroline (0.3 mmol), PPh₃ (0.04 mmol), molecular sieves (3 Å, 250 mg) | 66 |
| 57 | 2-fluorophenyl | 4-methylphenyl | Cs₂CO₃ (1.2 mmol), CuCl (0.10 mmol), Pd(acac)₂ (0.02 mmol), 1,10-phenanthroline (0.2 mmol), PPh₃ (0.06 mmol), molecular sieves (3 Å, 250 mg) | 67 |
| 58 | 2-thienyl | 4-methylphenyl | K₂CO₃ (1.2 mmol), CuCl (0.10 mmol), Pd(acac)₂ (0.02 mmol), 1,10-phenanthroline (0.1 mmol), PPh₃ (0.06 mmol), molecular sieves (3 Å, 250 mg) | 65 |
| 59 | styryl (PhCH=CH-) | 4-methylphenyl | see Example 56 | 91 |
| 60 | 2-formylphenyl (2-CHO-C₆H₄-) | 4-methylphenyl | see Example 56 | 28 |
| 61 | 2-nitrophenyl | 4-(methylthio)phenyl (-C₆H₄-SCH₃) | see Example 24 with 0.1 mmol of CuI | 98 |
| 62 | 2-nitrophenyl | 9-phenanthryl | see Example 24 | 99 |
| 63 | 2-nitrophenyl | 4-(trifluoromethyl)phenyl (-C₆H₄-CF₃) | see Example 24 | 93 |
| 64 | 2-nitrophenyl | 4-cyanophenyl (-C₆H₄-CN) | see Example 24 | 93 |

-continued

| | R | R¹ | Conditions | Yield (%) |
|---|---|---|---|---|
| 65 | 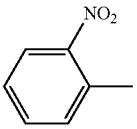 | 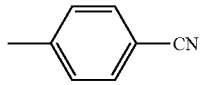 | see Example 24 from the aryl chloride | 96 |
| 66 | 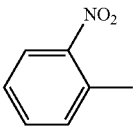 | 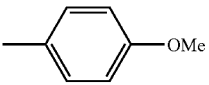 | see Example 24 | 68 |
| 67 | 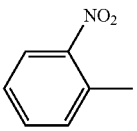 | 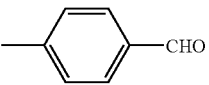 | see Example 24 | 78 |
| 68 | 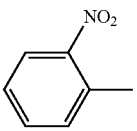 |  | see Example 24 | 97 |
| 69 | 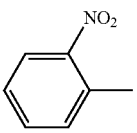 | 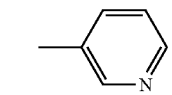 | see Example 24 | 98 |
| 70 | 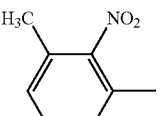 |  | see Example 24 | 74 |
| 71 | 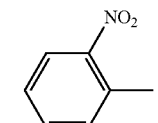 |  | see Example 24 | 77 |

The invention claimed is:

1. A process for decarboxylating and C—C bond formation comprising reacting carboxylic acid salts with carbon electrophiles in the presence of a catalyst system to achieve decarboxylating C—C bond forming cross-coupling, said catalyst system comprising first and second transition metal compounds and one or more ligands;

wherein the carboxylic acid salts are selected from the group consisting of carboxylic acid salts of the Formula 1 where n, m, q, p are numbers from 1 to 6 and r is a number from 0 to 6; $M^{(m+)}$ is a cation of a metal selected from the group consisting of Li, Na, K, Mg, Ca, B, Al, Ag, Cu, Mn, Fe, Co, Ni, Mo, and Ru; R is selected from the group consisting of linear, branched and cyclic $C_2$-$C_{20}$-alkenyl, and also $C_6$-$C_{20}$-aryl and heteroaryl selected from the group consisting of pyridinyl, pyrimidinyl, pyridazinyl, pyrazinyl, triazinyl, tetrazinyl, pyrrolyl, pyrazolyl, isoxazolyl, imidazolyl, oxazolyl, thiazolyl, thiophenyl and furanyl, and may in turn bear further substituents selected from the group consisting of linear, branched and cyclic $C_1$-$C_{10}$-alkyl, linear, branched and cyclic $C_2$-$C_{20}$-alkenyl, and also $C_6$-$C_{10}$-aryl and heteroaryl, linear, branched and cyclic $C_1$-$C_{10}$-alkyloxy or $C_1$-$C_{10}$-aryloxy, linear, branched and cyclic $C_1$-$C_{10}$-alkyl- or $C_1$-$C_{10}$-arylaminocarbonyl, linear, branched and cyclic $C_1$-$C_{10}$-acyl, linear, branched and cyclic $C_1$-$C_{10}$-dialkylamino, $C_1$-$C_{10}$-arylamino, formyl, thio, hydroxyl, carboxyl, nitro, cyano, nitroso, and halogens; and $Y^{(p-)}$ is an anion:

Formula 1

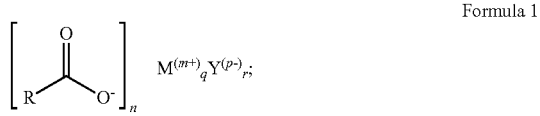

wherein the carbon electrophiles are selected from the group consisting of carbon electrophiles of the formula formula $R^1$—X where $R^1$ is selected from the group consisting of linear, branched and cyclic $C_2$-$C_{20}$-alkenyl, and also $C_6$-$C_{20}$-aryl and heteroaryl selected from the group consisting of pyridinyl, pyrimidinyl, pyridazinyl, pyrazinyl, triazinyl, tetrazinyl, pyrrolyl, pyrazolyl, isoxazolyl, imidazolyl, oxazolyl, thiazolyl, thiophenyl and furanyl, and may in turn bear further substituents from the group of linear, branched and cyclic $C_1$-$C_{10}$-alkyl, linear, branched and cyclic $C_2$-$C_{20}$-alkenyl, and also $C_6$-$C_{10}$-aryl and heteroaryl, linear, branched and cyclic $C_1$-$C_{10}$-alkyloxy or $C_1$-$C_{10}$-aryloxy, linear, branched and cyclic $C_1$-$C_{10}$-alkyl- or $C_1$-$C_{10}$-arylaminocarbonyl, linear, branched and cyclic $C_1$-$C_{10}$-acyl, linear, branched and cyclic $C_1$-$C_{10}$-dialkylamino, $C_1$-$C_{10}$-arylamino, formyl, oxo, thio, hydroxyl, carboxyl, nitro, cyano, nitroso, and halogens; and X is selected from the group consisting of halides selected from the group consisting of I, Br, and Cl, and pseudohalides selected from the group consisting of toluenesulfonate, methylsulfonate, trifluorosulfonate, trifluoroacetate, carboxylate and $[N_2]^+$;

wherein the first transition metal compound is selected from the group consisting of copper compounds;

wherein the second transition metal compound is selected from the group consisting of palladium compounds;

wherein the one or more ligands are selected from the group consisting of amines, phosphines, N-heterocyclic carbenes, nitriles and olefins;

provided that if R represents aryl or heteroaryl, then $R^1$ is not vinyl.

2. The process as claimed in claim 1, wherein the second transition metal compound is palladium(II) acetylacetonate.

3. The process as claimed in claim 1, wherein a cyclic amine is used as the ligand.

4. The process as claimed in claim 1, wherein the ligand is an optionally substituted chelating cyclic amine selected from the group consisting of phenanthroline, bipyridine and terpyridine.

5. The process as claimed in claim 1, which further comprises employing mutually independent amounts of the two catalysts of from 0.001 mol % to 100 mol % based on the carbon electrophile.

6. The process as claimed in claim 1, which further comprises employing mutually independent amounts of the two catalysts of from 0.01 mol % to 5 mol % based on the carbon electrophile.

7. The process as claimed in claim 1, wherein the substituent R is selected from the group consisting of linear, branched and cyclic $C_2$-$C_{20}$-alkenyl, and also $C_6$-$C_{20}$-aryl and heteroaryl selected from the group consisting of pyridinyl, pyrimidinyl, pyridazinyl, pyrazinyl, triazinyl, tetrazinyl, pyrrolyl, pyrazolyl, isoxazolyl, imidazolyl, oxazolyl, thiazolyl, thiophenyl and furanyl, and may in turn bear further substituents selected from the group consisting of linear, branched and cyclic $C_1$-$C_{10}$-alkyl, linear, branched and cyclic $C_2$-$C_{20}$-alkenyl, and also $C_6$-$C_{10}$-aryl and heteroaryl, linear, branched and cyclic $C_1$-$C_{10}$-alkyloxy or $C_1$-$C_{10}$-aryloxy, linear, branched and cyclic $C_1$-$C_{10}$-alkyl- or $C_1$-$C_{10}$-arylaminocarbonyl, linear, branched and cyclic $C_1$-$C_{10}$-acyl, linear, branched and cyclic $C_1$-$C_{10}$-dialkylamino, arylamino, formyl, thio, hydroxyl, carboxyl, nitro, cyano, nitroso, and halogens.

8. The process as claimed in claim 1, wherein the substituent $R^1$ of the carbon electrophile is selected from the group consisting of linear, branched and cyclic $C_2$-$C_{20}$-alkenyl, and also $C_6$-$C_{20}$-aryl and heteroaryl selected from the group consisting of pyridinyl, pyrimidinyl, pyridazinyl, pyrazinyl, triazinyl, tetrazinyl, pyrrolyl, pyrazolyl, isoxazolyl, imidazolyl, oxazolyl, thiazolyl, thiophenyl and furanyl, and may in turn bear further substituents selected from the group consisting of linear, branched and cyclic $C_1$-$C_{10}$-alkyl, linear, branched and cyclic $C_2$-$C_{20}$-alkenyl, and also $C_6$-$C_{10}$-aryl and heteroaryl, linear, branched and cyclic $C_1$-$C_{10}$-alkyloxy or $C_1$-$C_{10}$-aryloxy, linear, branched and cyclic $C_1$-$C_{10}$-alkyl- or $C_1$-$C_{10}$-arylaminocarbonyl, linear, branched and cyclic $C_1$-$C_{10}$-acyl, linear, branched and cyclic $C_1$-$C_{10}$-dialkylamino, $C_1$-$C_{10}$-arylamino, formyl, oxo, thio, hydroxyl, carboxyl, nitro, cyano, nitroso, and halogens.

9. The process as claimed in claim 1, which is carried out at a reaction temperature of from 80° C. to 200° C.

10. The process as claimed in claim 1, which is carried out at a reaction temperature of from 120° C. to 160° C.

11. The process as claimed in claim 1, wherein traces of water are removed during the reaction.

12. The process as claimed in claim 1, wherein the carbon electrophile is a carbonyl derivative selected from the group consisting of carbonyl chloride, carboxylic anhydride, aldehyde, ketone, ester, α,β-unsaturated aldehyde, α,β-unsaturated ketone, and α,β-unsaturated ester.

\* \* \* \* \*